United States Patent
Shah et al.

(10) Patent No.: US 7,600,413 B2
(45) Date of Patent: Oct. 13, 2009

(54) GAS CHROMATOGRAPHY SYSTEM ARCHITECTURE

(75) Inventors: Jagdish Shah, Southington, CT (US);
Neil William Bostrom, Cambridge, MA (US); Hua Chen, Ridgefield, CT (US);
Shigeo Daito, Lexington, MA (US);
Edward Harrigan, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 110 days.

(21) Appl. No.: 11/564,430

(22) Filed: Nov. 29, 2006

(65) Prior Publication Data
US 2008/0121016 A1    May 29, 2008

(51) Int. Cl.
*G01N 30/04* (2006.01)
(52) U.S. Cl. .................................. 73/23.42; 73/23.35
(58) Field of Classification Search ............... 73/23.35, 73/23.42
See application file for complete search history.

(56) References Cited

U.S. PATENT DOCUMENTS

| | | | |
|---|---|---|---|
| 3,165,147 A | | 1/1965 | Roof et al. |
| 3,360,904 A | | 1/1968 | Perkins et al. |
| 3,538,744 A | * | 11/1970 | Karasek ..................... 73/23.39 |
| 4,176,542 A | * | 12/1979 | Redding ..................... 73/23.25 |
| 4,935,040 A | * | 6/1990 | Goedert ..................... 73/23.22 |
| 6,074,461 A | * | 6/2000 | Wilson ........................ 96/102 |
| 2003/0233862 A1 | | 12/2003 | Wise et al. |
| 2006/0008382 A1 | * | 1/2006 | Salamitou et al. ............ 422/57 |
| 2007/0125233 A1 | * | 6/2007 | Bostrom et al. .............. 96/101 |

FOREIGN PATENT DOCUMENTS

| | | |
|---|---|---|
| EP | 0602924 A2 | 6/1994 |
| EP | 0708331 B1 | 3/2004 |
| WO | 9604547 | 2/1996 |
| WO | 0228532 A2 | 4/2002 |

* cited by examiner

*Primary Examiner*—Daniel S Larkin
(74) *Attorney, Agent, or Firm*—James McAleenan; Jody Lynn DeStefanis; Dale Gaudier (57) ABSTRACT

A self-contained micro-scale gas chromatography system that includes a plurality of gas chromatography components arranged on a micro-fluidic platform with nearly zero dead volume "tubeless" fluidic connections for the gas chromatography components. The micro-fluidic platform includes a plurality of flow channels that provide fluid flow paths for a sample, carrier gas and waste gas through and among the micro-fluidic platform and the plurality of gas chromatography components. The system may also include an on-board supply of carrier gas and on-board waste management, as well as a thermal management scheme making the system suitable for use in oil and gas wells and also other remote environments.

23 Claims, 8 Drawing Sheets

GAS CHROMATOGRAPHY SYSTEM ARCHITECTURE

BACKGROUND

1. Field of Invention

The present invention relates to gas chromatography systems and, more particularly, to small-scale systems that may be suitable for operation in various environments.

2. Discussion of Related Art

Gas chromatography uses chromatographic columns to separate molecular species within a sample fluid and thereby to extract information about the sample fluid. A chromatographic column has a stationary phase fixed inside the column and a mobile phase which is a carrier gas, such as, helium that flows through the column. The sample is collected, injected into the column and then transported by the carrier gas into and through the column. If the sample is in a liquid state, the sample may first be injected into a vaporization chamber to be vaporized then transported through the column. As a sample progresses through the column, the individual molecular components are slowed down based on their affinity to the stationary phase. At the outlet of the column, a detector measures the quantity of each component as it exits the column. The calibrated retention time, i.e., the time a component spends in the column, identifies the component.

Conventional gas chromatography apparatus is built around a standard chromatographic column and injector which, when packaged with thermal management apparatus, becomes bulky. The larger the column and flow channels, the greater the rate of carrier gas consumption. As a result, for conventional systems, a relatively large supply of carrier gas is needed. Typically, chromatographic analysis of a sample using a traditional system is done in a laboratory or other environment where a large reservoir of carrier gas is present.

Boreholes are typically small diameter holes having a diameter of approximately five (5) inches or less, although open holes may have larger diameters. In addition, vibrations and typically high temperature (about 200 degrees Celsius) and high pressure environments are experienced down-hole, adding further constraints to the design of a system suitable for down-hole operation. Furthermore, the temperature of components of a chromatogram should be controlled and monitored accurately, which is difficult in a down-hole environment. Thus, given the space and other constraints of down-hole environments, the use of traditional gas chromatography devices down-hole would be challenging.

There have been some attempts to develop smaller gas chromatography devices. For example various companies have introduced portable gas chromatography apparatus employing a limited micro-scale technology. However, none have been designed for down-hole applications. One such example system is that produced by SLS MICRO TECHNOLOGY GmbH. The SLS unit incorporates a micro-scale column and detector with a motorized sliding injector of about 1 inch by 1 inch and about 1.5 inches in length. However, the SLS device lacks the inclusion of high-pressure sampling and thermal management requirements to operate in a high temperature (e.g., about 200° C.) down-hole environment. The SLS unit also lacks an on-board supply of carrier gas and means of waste disposal that would be desirable, or even necessary, for down-hole applications. Furthermore, the SLS system uses a glued component layout consisting of fused silica tubes to provide fluidic interconnections which may not be suitable for high-temperature environments.

Another example is a system produced by the C2V (Concept to Volume) company based in the Netherlands. The C2V unit includes a micro-scale injector and detector. However, the unit uses traditional columns housed in a heated canister. The injector, although micro-scale, needs an external supply of regulated fluidic pressure to operate various micro-valves and is not designed to operate in a high temperature and pressure environment. The fluidic connections are achieved by glued capillary tubes which may be unsuitable for down-hole applications or other high temperature environments. In addition, the C2V unit does not include an on-board supply of carrier gas and waste disposal is not addressed. The flow rate requirements are much larger than the SLS device, and would require considerably larger volumes of carrier gas. The C2V device also does not have thermal management and operates in isothermal mode only, that is, all components are operated at same temperature. Neither the SLS device nor the C2V device has a tool architecture that is functionally suitable for down-hole applications.

SUMMARY OF INVENTION

Various aspects and embodiments of the invention are directed to a gas chromatography system that includes micro-scale components deployed in a manner suitable for down-hole conditions. In order to perform chromatographic analyses down-hole or in other non-laboratory environments such as, for example, underwater environments, other underground (i.e., non-oil-well) locations or space-limited environments or non-Earth environments (e.g., in space or on other planets), the system may be self-contained, including an on-board supply of carrier gas and on-board waste disposal. Further, the small size of systems according to embodiments of the invention may provide critical advantages that improve operability and reliability of gas chromatographic analysis, particularly in down-hole environments. For example, the small size of embodiments of the system may facilitate thermal management, as discussed below.

According to one embodiment, a gas chromatography apparatus may comprise a micro-fluidic platform comprising a plurality of micro-channels disposed thereon, an injector coupled to the micro-fluidic platform and constructed and arranged to provide a sample for analysis, one or more gas chromatography columns coupled to the injector via the micro-fluidic platform and constructed and arranged to receive the sample from the injector and to produce an output dependent on a chemical composition of the sample. The apparatus may further comprise one or more detectors coupled to the gas chromatography column(s) and constructed and arranged to receive the output from the gas chromatography column(s), as well as a housing substantially surrounding and enclosing the micro-fluidic platform, the injector, the gas chromatography column(s) and the detector(s), wherein the plurality of micro-channels provide flow channels for the sample and the output from the gas chromatography column(s). In one example, at least one of the injector, the gas chromatography column(s) and the detector(s) is implemented at the micro-scale.

According to another embodiment, a micro-scale gas chromatography system may comprise a plurality of gas chromatography components, and a micro-fluidic platform coupled to the plurality of gas chromatography components to interconnect the plurality of gas chromatography components, wherein the micro-fluidic platform comprises a plurality of flow channels that provide fluid flow paths for a sample, carrier gas and waste gas through and among the micro-fluidic platform and the plurality of gas chromatography components. In one example, the plurality of gas chromatography components includes an injector, at least one gas chromatography column and at least one detector. The system may further comprise means for individually controlling operating temperatures of at least some of the plurality of gas chromatography components, including, for example, a heater disposed adjacent at least one of the injector, the gas chromatography column and the detector, and optionally thermal traps and thermal stops disposed about the plurality of gas chromatography components to thermally isolate the plurality of components from one another.

BRIEF DESCRIPTION OF THE DRAWINGS

Various aspects and embodiments of the invention are described below with reference to the accompanying figures. In the drawings, which are not intended to be drawn to scale, each identical or nearly identical component that is illustrated in various figures is represented by a like numeral. For purposes of clarity, not every component may be labeled in every drawing. In the drawings.

DETAILED DESCRIPTION

Embodiments of the invention and aspects thereof are directed to a gas chromatography apparatus and system that incorporates micro-scale components and may be suitable for use in a variety of environments. Traditionally, gas chromatographic analysis is performed on the surface of the earth, usually in a laboratory or similar environment. A sample may be collected at a remote location or sample site, for example, an underground or underwater location, and then returned to a testing facility, such as a laboratory, for chromatographic analysis. As discussed above, although there have been some developments of portable gas chromatography systems, none have been suitable for down-hole applications. Therefore, to address these and other limitations in the prior art, aspects and embodiments of the invention are directed to a gas chromatography system having an architecture that allows for down-hole operation. For example, boreholes are typically small diameter holes having a diameter of approximately five (5) inches or less. Therefore, according to one embodiment, a gas chromatography system that includes components arranged in a tubular housing, the housing having as small an outer diameter as feasible, may be well suited to down-hole applications. In addition, high temperature and high pressure are generally experienced in down-hole environments. Therefore, the components and/or housing of the apparatus should be able to accommodate these conditions. For example, in one embodiment, a gas chromatography apparatus may include thermal management techniques. In addition, a gas chromatography apparatus according to embodiments of the invention may be a self-contained unit including an on-board supply of carrier gas and on-board waste management. These and other features and aspects of embodiments gas chromatography apparatus according to embodiments of the invention are discussed in more detail below with reference to the accompanying figures.

It is appreciated that this invention is not limited in its application to the details of construction and the arrangement of components set forth in the following description or illustrated in the drawings. The invention is capable of other embodiments and of being practiced or of being carried out in various ways. For example, it is to be appreciated that the gas chromatography apparatus described herein is not limited to use in boreholes and may be used in a variety of environments and application such as, for example, other underground applications, underwater and/or space applications. Examples of specific implementations are provided herein for illustrative purposes only and are not intended to be limiting. In particular, acts, elements and features discussed in connection with one embodiment are not intended to be excluded from a similar role in other embodiments. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

Figure 1:
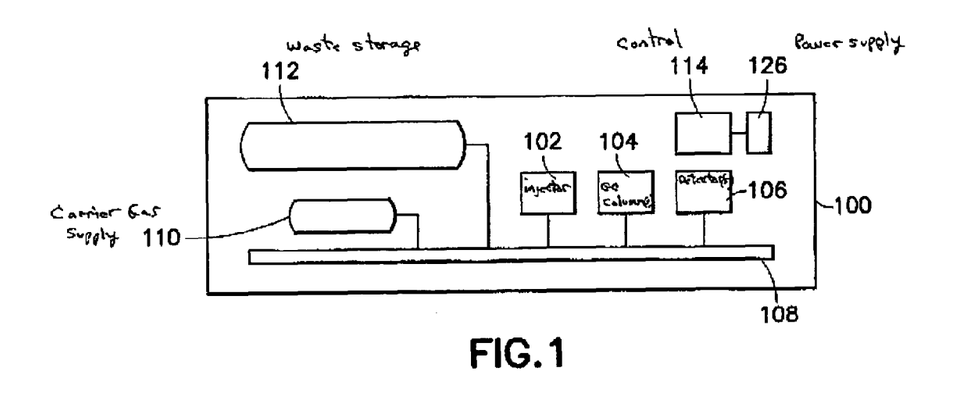
FIG. 1 is a block diagram illustrating one embodiment of a gas chromatography system according to the invention.

Referring to FIG. 1, there is illustrated a block diagram of one embodiment of a gas chromatography (GC) system according to the invention. The system may comprise a plurality of components contained within a housing 100. These components may include, for example, an injector 102, one or more gas chromatography columns 104 and one or more detectors 106. These components are collectively referred too as GC components and are described in more detail below. These components may be coupled to one another either directly or via a micro-fluidic platform 108 which is also discussed in detail below. In addition, the system may include a power supply 126 and control components 114. In one example, the power supply may include a wire line that may connect the gas chromatography system to an external source of power (e.g., a generator or public electricity supply). In another example, particularly where several of the GC components may be micro-scale components, the power requirements may be sufficiently to small to allow battery operation and the power supply 126 may thus include one or batteries. These batteries may be, for example, Lithium Thionel Chloride batteries rated for high temperature environments. As discussed above, the system may also include a carrier gas supply 110 as well as a waste storage component 112. Having an on-board supply of carrier gas may allow the GC system to be operated down-hole (or in another remote environment)

without requiring connection to an external supply of gas. In a down-hole or other pressurized environment (e.g., deep underwater locations), it may be difficult, if not impossible, to vent waste gas to outside of the gas chromatography system due to high ambient pressure. Therefore, the on-board waste storage component 112 may be particularly desirable. By making at least some of the system components micro-scale components, a chromatography device small enough to comply with the space constraints of down-hole environments may be realized.

It is to be appreciated that although embodiments of chromatography systems may be referred to herein as micro-scale systems, not all of the components are required to be micro-scale and at least some components may be meso-scale or larger. This is particularly the case where the device is intended for use in environments where the space constraints are not as tight as for down-hole applications. As used herein, the term "micro-scale" is intended to mean those structures or components having at least one relevant dimension that is in a range of a few micrometers to approximately one (1) millimeter (mm). In order to achieve these scales, manufacturing technologies such as silicon micro-machining, chemical etching and other methods known to those skilled in the art may be used. Thus, for example, a "micro-scale" gas chromatography column may be constructed using a silicon wafer into which are etched or machined very small channels of the micrometer-scale width. Although the overall size of such a column may be a few centimeters, (in width and/or length), a relevant feature, namely, the channels, are not only micro-scale, but also may be manufactured using micro-machining (or chemical etching) techniques. Therefore, such a column may be referred to as a micro-scale column. Such columns have very low mass when packaged and may therefore allow for easier thermal management compared to traditionally packaged columns. By contrast, "meso-scale" components of a gas chromatograph, e.g., a column, injector and/or detector. may have relevant dimensions that may be between several micrometers and a few millimeters and may be made using traditional manufacturing methods such as milling, grinding, glass and metal tube drawing etc. Such components tend to be bulkier than components that may be considered "micro-scale" components. Thus, for example, a traditional gas chromatography column may be made of a stainless steel or glass capillary tube having an inside diameter on the order of about 100 micrometers, but a length of several meters. A meso-scale injector, for example, may also be made using traditional manufacturing techniques and may measure a few tens of millimeters in size. Thus, the terms micro-scale and meso-scale relate not only to the size of relevant dimensions or parameters of components but also to the manufacturing techniques used to produce the components. As known to those skilled in the art, there are no defined boundaries between these terms and they do overlap. However, the distinction between micro-scale and meso-scale, as discussed above, refers to both the manufacturing technique and the length scale.

As discussed above, a gas chromatography apparatus according to embodiments of the invention may comprise an injector 102, at least one column 104 and at least one detector 106 interconnected via a micro-fluidic platform 108. The micro-fluidic platform may include flow channels that provide fluid connections between the various GC components, as discussed further below. It is to be appreciated that various embodiments of the apparatus may include one or more columns that may be disposed in a parallel or series configuration. In a parallel configuration, a sample may be directed into multiple columns at the same time using, for example, a valve mechanism that couples the columns to the micro-fluidic platform. The output of each column may be provided to one or more detectors. For example, the same detector may be used to analyze the output of multiple columns or, alternatively, some or all of the columns may be provided with a dedicated detector. In another example, multiple detectors may be used to analyze the output of one column. Multiple detectors and/or columns may be coupled together in series or parallel. In a series configuration of columns, the output of a first column may be directed to the input of a second column, rather than to waste. In one example, a detector may be also positioned between the two columns as well as at the output of the second column. In another example, a detector may be positioned only at the output of the last column of the series. It is to be appreciated that many configurations, series and parallel, are possible for multiple columns and detectors and that the invention is not limited to any particular configuration or to the examples discussed herein.

In one embodiment of a micro-scale gas chromatograph, some or all of the GC components may be MEMS (Micro-Electro-Mechanical Systems) devices. Such devices may be small and thus appropriate for a system designed to fit within a small housing 100 suitable for down-hole deployment. In addition, such devices may be easily coupled to the micro-fluidic platform 108. In one example, some or all of the three components may be MEMS devices that are approximately two (2) centimeters (cm) by 2 cm by 1-2 mm thick. Arranged linearly, as shown, for example, in FIG. 1, these devices could be easily be housed within a cylinder having an inner diameter of about two (2) inches or less and a length of about four (4) inches. However, it is to be appreciated that the injector 102, column 104 and detector 106 need not be discrete devices and also need not be linearly arranged within the housing 100. Many other configurations are also possible and are considered included in this disclosure. In addition, many variations on the size and thickness of the devices are also possible and the invention is not limited to the specific example given herein.

Figure 2A:
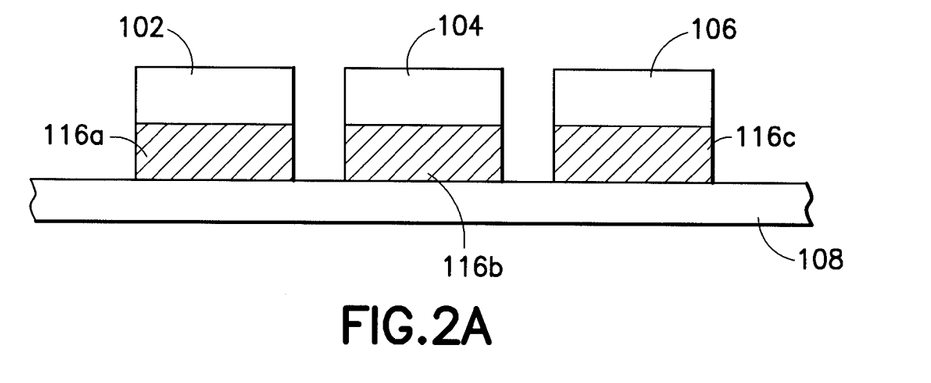
FIG. 2A is a block diagram of one example of component layout for a gas chromatography apparatus according to aspects of the invention.
Figure 2B:
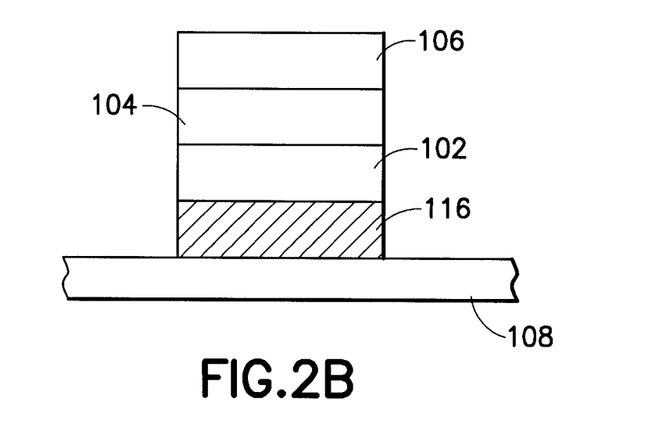
FIG. 2B is a block diagram of another example of component layout for a gas chromatography apparatus according to aspects of the invention.
Figure 2C:
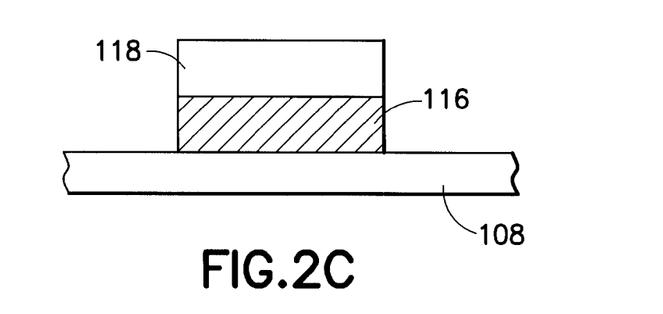
FIG. 2C is a block diagram of another example of component layout for a gas chromatography apparatus according to aspects of the invention.

For example, referring to FIGS. 2A-2C, there are illustrated three examples of arrangements of the injector 102, column 104 and detector 106. In FIG. 2A, the GC components are illustrated in a linear arrangement, similar to that shown in FIG. 1. Such a linear configuration may be advantageous when it is desirable to keep the inner diameter of the housing as small as possible and where the length of the housing is less critical. This configuration may also have the advantage of allowing each discrete device to have individual thermal management including, for example, individual heating devices 116a, 116b, and 116c, as shown. Therefore, this linear configuration may be preferred in application where the injector, column(s) and detector(s) are to be operated at different temperatures. In the illustrated example, the heating elements are shown positioned between the respective component and the micro-fluidic platform 108; however, it is to be appreciated that the invention is not limited to the illustrated arrangement. Referring to FIG. 2B, the injector 102, column 104 and detector 106 are illustrated in a stacked arrangement, one on top of the other. Such a stacked arrangement may be preferable if there is a need or desire to shorten the length of the housing. For example, the stacked components, along with other components making up the gas chromatograph, may fit within a housing having an inner diameter of less than about 2 inches and a length of about 1.5 inches. In another embodiment, illustrated in FIG. 2C, integrated MEMS device 118 may contain an injector, column and detector. In one example, such an integrated MEMS device may be less than about 2 cm by about 5 cm by about 1 to 2 mm in height. The stacked and integrated embodiments shown in FIGS. 2B and 2C may be particularly suitable for isothermal analysis where all active components are held at the same temperature. In these examples, one heater 116 may suffice for all of the injector, column and detector components.

According to one embodiment, a micro-scale chromatograph according to aspects of the invention may comprise one or more components at the micro-fluidic scale, wherein the flow channels are very small. For example, in one embodiment, the flow channels may be on the order of about sixty (60) microns. Volumetric flow rates of carrier gas through the flow channels scale approximately as the square of the effective diameter of the channel. Therefore, a micro-scale gas chromatography apparatus may inherently require a significantly smaller supply of carrier gas when compared to a meso-scale or larger scale system. In one example, a micro-scale gas chromatography apparatus may consume carrier gas at a rate five (5) or even ten (10) times slower than a traditional, larger gas chromatography system that includes much larger flow channels. This may be advantageous in that both the carrier gas supply 110 and waste storage component 112 (see FIG. 1) may be comparatively smaller as they may contain a smaller volume of gas. For example, assuming that the carrier gas consumption for a micro-scale gas chromatograph is on the order of about 100 microliters per minute ($\mu$L/min), for a 1000-minute service down-hole, 100 milliliters (mL) of carrier gas may be required. Assuming that the analysis is performed at near-atmospheric pressure (approximately 15 psi), a waste storage container 112 of about 100 mL would be needed. In one embodiment, the carrier gas supply may be stored in a high-pressure (e.g., about 1000 psi) container 110 and thus, the size of the container 110 may be extremely small.

Containers of these and similar sizes may easily fit within a housing 100 that is formed as a slender cylinder. For example, a cylindrical housing 100 that has an inner diameter of about two (2) inches or less and a length of about five (5) inches or less may contain the above-mentioned waste storage container 112, carrier gas supply container 110. In one example, the housing 100 may be a cylinder having an inner diameter of approximately 1.75 inches and a length of about five (5) inches. A housing of this or similar size may fit comfortable down a borehole or into another narrow opening, as discussed above. In one example, the gas chromatography analysis may be performed at higher than atmospheric pressure. In this case, the waste gas may be compressed, thus needing an even smaller waste container 112. Of course, it will be appreciated that the amount of carrier gas needed, and thus also the sizes of the carrier gas and waste storage containers, may vary depending on the actual flow rates in the system as well as the desired length of service time. Accordingly, the invention is not limited to the specifics of the examples discussed herein which are given for the purpose of illustration and are not intended to be limiting.

Figure 3:
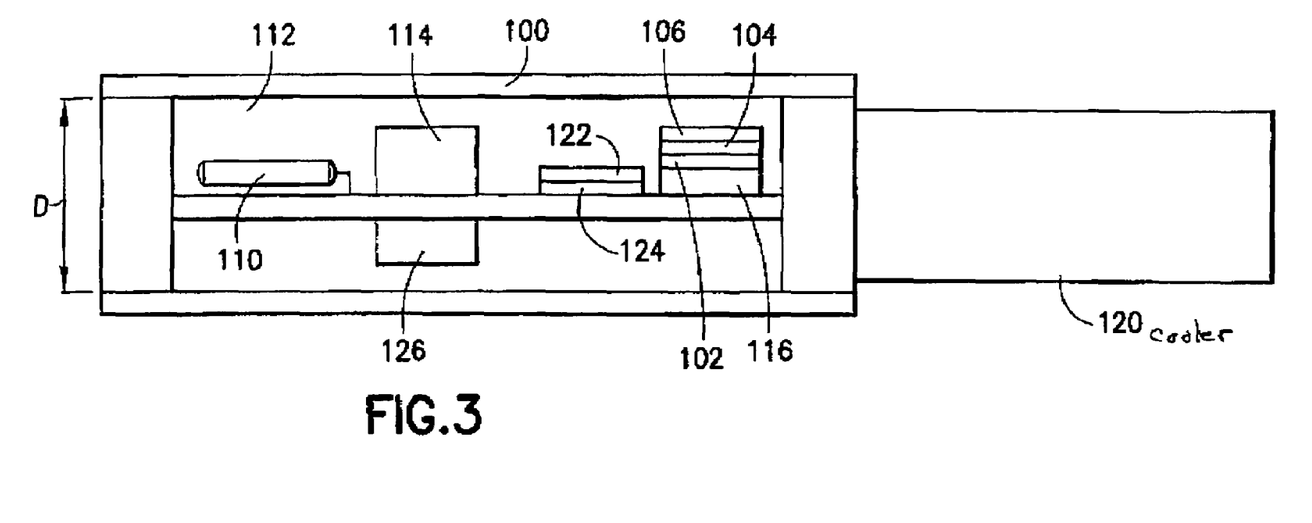
FIG. 3 is a block diagram of another embodiment of a gas chromatography system according to the invention.

Referring to FIG. 3, there is illustrated a block diagram of another embodiment of a gas chromatography apparatus according to the invention. In this embodiment, the injector 102, column 104 and detector 106 are shown in a stacked arrangement, one on top of the other. However, it is to be appreciated than any of the above-mentioned configurations may be used. Also shown are some thermal management components including the heater(s) 116 discussed above and a cooler 120. These components are discussed in more detail below. In the illustrated embodiment, the housing 100 that contains the GC components, the micro-fluidic platform 108, carrier gas container 110 and other components, may also serve as the waste storage container 112. This may eliminate the need for a separate waste storage container which may reduce the overall size of the system. In one example of this embodiment, the housing 100 may be a cylinder that has an inner diameter D of about two (2) inches and a length of about eight (8) inches.

According to some embodiments of the invention, a gas chromatography system may also include a sampler 122. Before a fluid to be analyzed (referred to herein as a "formation fluid") can be introduced into the gas chromatography apparatus, a sample of the formation fluid may be extracted from its environment (e.g., from a rock formation in the case of boreholes). Thus, a self-contained gas chromatography system may include the sampler 122 to perform this extraction/sampling. In down-hole environments, the formation fluid may be at high pressure (e.g., about 20 Kpsi) and high temperature (up to about 200° C. or even higher). Traditional chromatographic methods require that the sample be de-pressurized, while carefully modulating its temperature to control the separation process. According to one embodiment, a micro-scale sampler can be may be integrated into the gas chromatography apparatus. The sampler 122 may be coupled to a heater 124 to achieve at least some temperature modulation. In one example, the sampler 122 may be a multi-stage sampler and phase separator. In this example, the sampler 122 may perform phase separation to eliminate water, which can deteriorate gas chromatographic analysis. Being at the microscale, the sampler may then isolate a minute quantity of formation fluid, for example, in the sub-micro liter or nano-liter range. Depressurization may be accomplished in an expansion chamber accompanied by appropriate temperature control to preserve the sample elution.

Figure 4A:
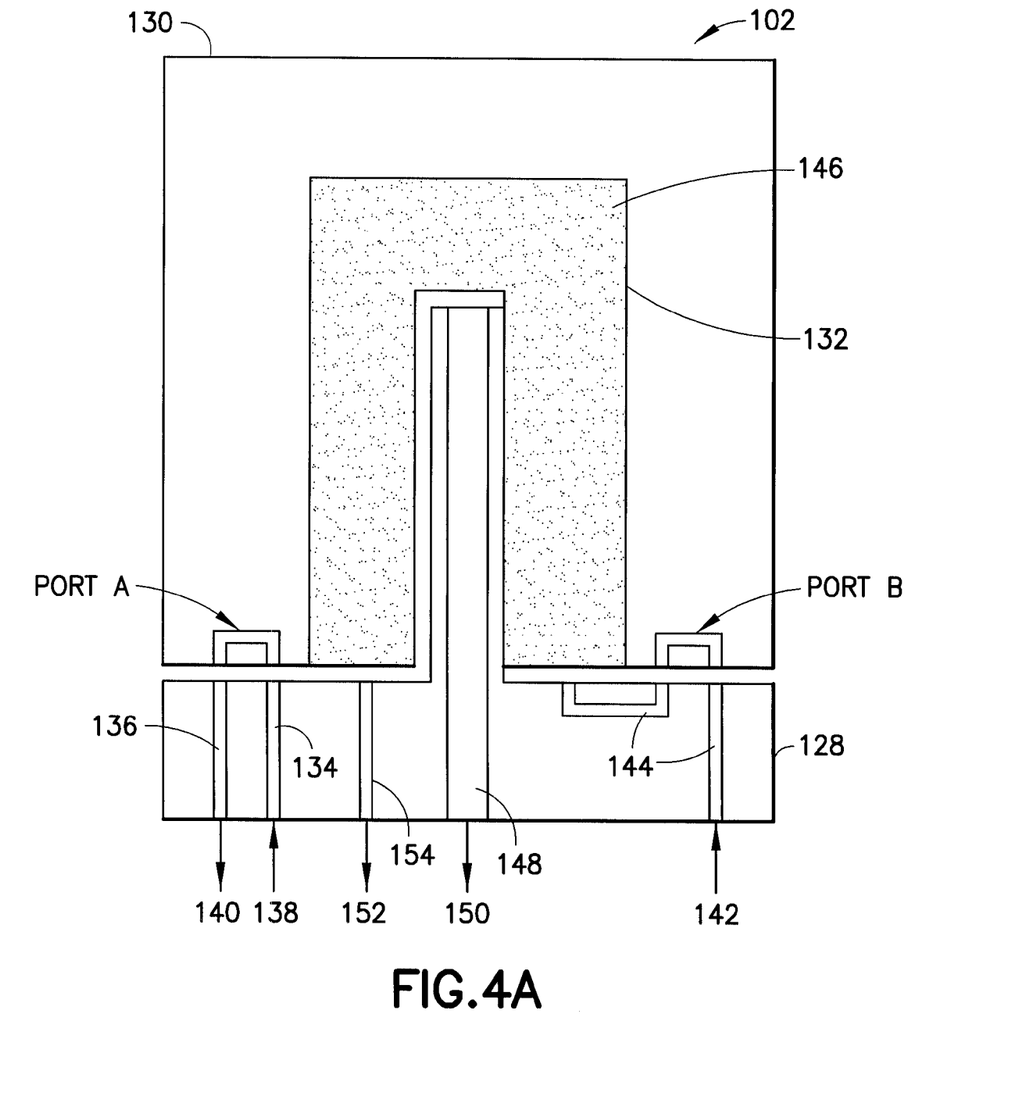
FIG. 4A is a diagram of one embodiment of an injector according to the invention.

According to one embodiment, depressurization may be accomplished by the injector 102. Referring to FIG. 4A, there is illustrated one example of an injector 102 according to an embodiment of the invention. The injector may be implemented at the micro-scale, but may also be a meso-scale or larger device. The injector 102 may comprise a stator 128 that is coupled to the sampler 122 (not shown) and to the micro-fluidic platform (not shown), and a rotor 130 coupled to the stator. The injector also comprises an expansion chamber 132. As discussed above, the sampler may collect a small sample of formation fluid and, in at least some embodiments, may separate water out from the sample of formation fluid. The remaining high pressure sample, indicated by arrow 138. may be supplied from the sampler through a flow channel 134 to Port A of the injector. When the injector is in a sampling state (shown in FIG. 4A), the sample may flow through Port A and back out of the injector via flow channel 136, indicated by arrow 140. Meanwhile, at Port B, carrier gas at low-pressure (indicated by arrow 142) may continuously flows into the vaporization chamber 132 via flow channel 144 and Port B.

Figure 4B:
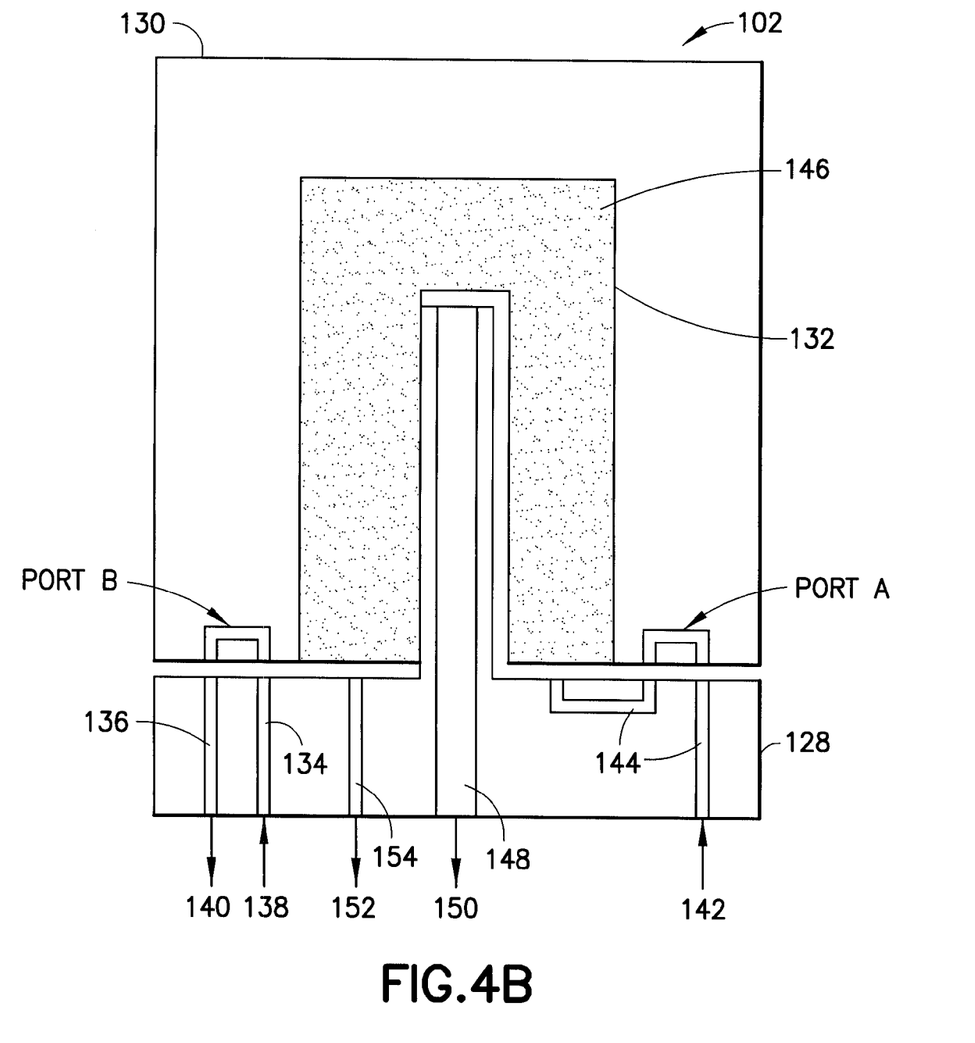
FIG. 4B is a diagram of the injector of FIG. 4A shown in an alternate state.

To inject a sample of formation fluid into the gas chromatography apparatus, the rotor may be turned by an external device (not shown) causing Port A to line up with flow channel 144 and Port B to line up with flow channels 134 and 136, as shown in FIG. 4B. The sample of formation fluid trapped in Port A may be flushed into the heated vaporization chamber 132 by the low-pressure carrier gas indicated by arrow 142. In one embodiment, the vaporization chamber 132 may be filled with a heated distribution material 146 such as, for example, silica glass wool. The distribution material 146 may provide a large surface area for sample vaporization and may disperse the injected sample in the flow of carrier gas. The high surface area distribution material may also trap any non-vaporized components, such as asphaltenes and sand which may be found in down-hole formation fluids, preventing these components from entering the column. A portion of the vaporized sample (indicated by arrow 150) may be forced into the column (not shown) via flow channel 148. The remaining vaporized sample and carrier gas (indicated by arrow 152) is waste and may exit the injector 102 via flow channel 154 to the waste storage container (not shown). The injector may thus provide a split injection scheme. The rotor may then be rotated back to the original position (illustrated in FIG. 4A) to collect a new sample of formation fluid at Port A.

Figure 5:
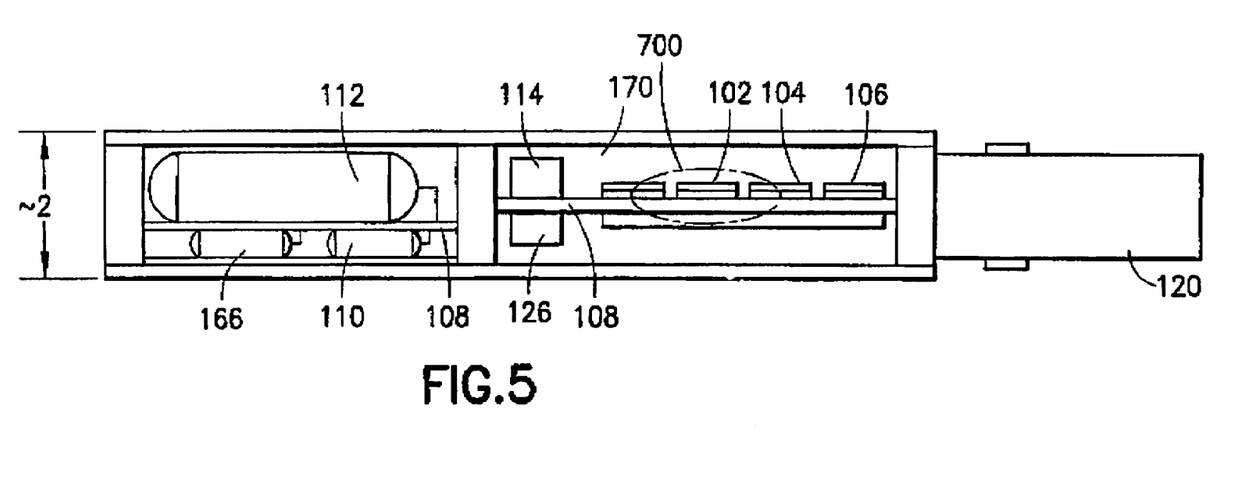
FIG. 5 is a block diagram of another embodiment of a gas chromatography system according to the invention.

According to one embodiment, a gas chromatography system may provide for in situ calibration of the gas chromatography apparatus. Referring to FIG. 5, there is illustrated another embodiment of a gas chromatography system according to aspects of the invention. In situ calibration may be achieved by including in the system an on-board supply of a calibration standard in container 166. The calibration standard may be a fluid having known constituents and known quantities of those constituents. The apparatus may be periodically calibrated by injecting a sample of the calibration standard into the column 104 instead of a sample of the formation fluid. Referring to FIG. 4A, a switching valve (not shown) external to the injector 102 may be attached to Port A. Thus, instead of arrow 138 indicating the injection of the sample of formation fluid, the arrow 138 indicates the flow of the calibration standard into Port A. This allows the calibration standard to be injected into the gas chromatography apparatus for calibration proposes. In one embodiment, the calibration standard may contain known concentrations of components that cover the designed analysis range of the column(s) 104. One or more directional valves may be incorporated into the flow channels to allow the flow path to be reversed to back-flush the system with carrier gas before and/or after calibration. As an alternative, a second small sample volume port, similar to Port A, on the rotary injector may allow the calibration standard to be injected into the gas chromatography apparatus without the need to flush the contents of Port A.

As discussed above, some or all of the components making up a gas chromatography apparatus according to embodiments of the invention may be implemented at the micro-scale. Particularly, referring again to FIGS. 1, 3 and 5, at least some of the injector 102, column(s) 104 and detector(s) 106 may be micro-scale devices and may be coupled to the micro-fluidic platform 108. In addition, as also discussed above, in at least some embodiments, these components may be MEMS devices. An advantage of the geometry of these components is the ability to achieve fluidic connections without the use of standard fluidic connections, such as tubes and fittings. Micro-scale devices lend themselves to near-zero dead volume connections, which may greatly affect the quality of chromatography. Elimination tubes and fittings may also facilitate thermal management as well as elimination of sources of contamination, as discussed further below.

Fluidic interconnections between various components of a gas chromatography apparatus can be significant sources of dead volumes and leakages, which can contaminate the sample. Particularly for chromatography systems which may need to operate in high pressure and temperature environments, these connections can pose significant design challenges. Moreover, even commercially available miniature connectors can add significant thermal mass compared to mass of micro-scale gas chromatography components, which can lead to difficulties in thermal management. As discussed above, the systems proposed by SLS and C2V use glued connections, wherein fused silica capillary tubing is glued into the gas chromatography components. Such connections do not allow part interchangeability and their performance at high temperature and pressure would be questionable. Therefore, according to one embodiment, a gas chromatography system including micro-scale GC components coupled to a micro-fluidic platform may allow reduction or even elimination such complications.

Figure 6:
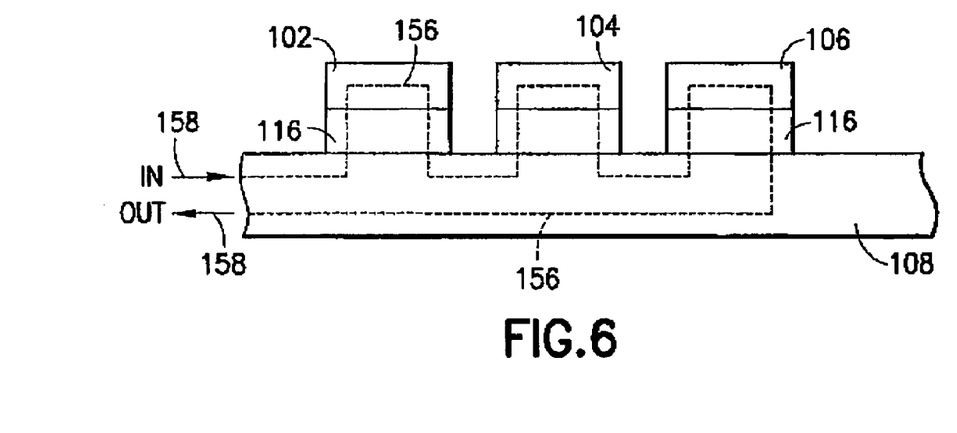
FIG. 6 is a block diagram illustrating a portion of a gas chromatography apparatus including fluidic channels, according to an embodiment of the invention.

Referring to FIG. 6, there is illustrated one example of a micro-fluidic platform 108 coupled to an injector 102, column 104 and detector 106 disposed in a linear arrangement. The micro-fluidic platform 108 includes micro-channels 156 for the flow paths (indicated by arrows 158) of the fluid sample, carrier gas and waste. The micro-fluidic platform 108 may be constructed by a variety of techniques. For example, silicon-glass substrates containing micro-channels may be anodically bonded to encapsulated complex fluid circuits that communicate with the GC components. The micro-flow channels may be etched using, for example, lithography-based techniques known in the art. Micro-fabrication techniques may allow positioning of GC components over the micro-fluidic platform with positional variation within a few microns such that the fluidic ports are well aligned while also providing a high degree of surface flatness. Either anodic bonding or "O"-rings can achieve sealing between the GC components and the platform. The assembly as described above, whether bonded or with O-rings, may inherently minimize dead volumes at connections through good alignment and elimination of large fluid connectors. This may result in better quality of GC analyses, since contamination between samples is eliminated.

According to another embodiment, the micro-fluidic platform may be manufactured out of metallic substrates that may be bonded by thermal diffusion. The micro-fluidic pathways within the substrate may be molded or machined by micro-EDM (electric discharge machining) processes. It may be apparent to those skilled in the art that other manufacturing options may also be used to construct the micro-fluidic platform. Thus, the invention is not limited to the specific examples given herein and this disclosure is intended to cover other such manufacturing techniques that may eliminate the use of tubing and related connectors and which achieves a direct flow path through the GC components via a common platform.

Furthermore, it is to be appreciated that a variety of materials may be used to form the micro-fluidic platform 108. In one example, particularly for a high temperature down-hole environment, materials with consistent thermal expansion properties, such as silicon-glass, may be chosen to prevent structural deterioration over repeated temperature cycles. Materials of construction, such as silicon-glass, non-reactive metals, etc. may have the added benefit that the chromatographic separation is not affected by local chemical activity, thus avoiding "active spots." In one example, a silicon-glass platform may be coated with, for example, an elastomer or thermoplastic to facilitate bonding of the GC components to the platform. Another example material that may be used for the platform is INVAR® (generically, FeNi36), an alloy of iron (64%) and nickel (36%) with added carbon and chromium, which has a low and well-controlled coefficient of thermal expansion. INVAR® is not inherently non-reactive; therefore, a platform that includes INVAR® may be coated to make it non-reactive. Any industry-standard coating may be used including, for example, TEFLON® or SILCOAT®.

Figure 7:
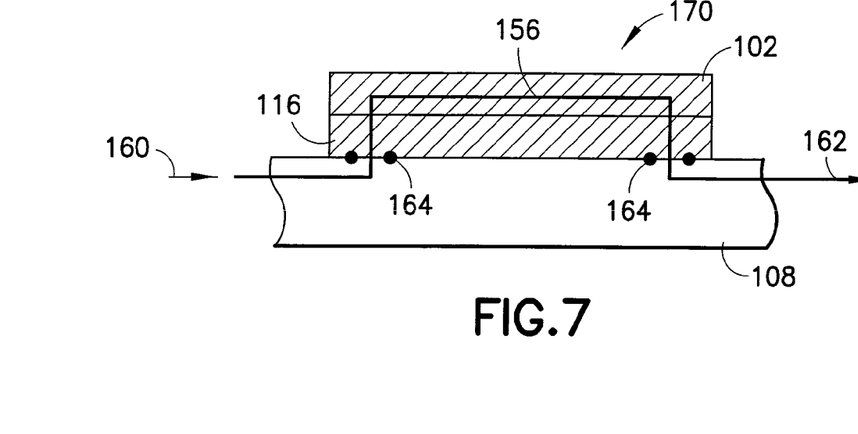
FIG. 7 is an enlarged view of the portion of the gas chromatography apparatus of FIG. 5 enclosed approximately by line 700.

Even a small amount of leakage across fluidic connectors can be detrimental to gas chromatographic analysis. According to aspects of the invention, a micro-fluidic platform may eliminate sources of leakage in several ways. For example, if the GC components are bonded to the platform as discussed above, leakage may be avoided because fluidic connectors may be eliminated. However, in some designs it may not be desirable to have a fully bonded construction for reasons of part interchangeability, replacement, and other practical considerations. Therefore, in another embodiment, "O"-ring seals may be used to connect the flow channels with the various GC components. Referring to FIG. 7, there is illustrated a portion (that surrounded by line 700 in FIG. 5) of the micro-fluidic platform 108 with flow channels 156 coupling to a GC component, for example, the injector 102. "O"-ring seals 164 are illustrated at the junction points between the injector 102 (or heater 116 if present) and the micro-fluidic platform 108.

As discussed above, the sample of formation fluid may be at a pressure much higher than atmospheric. Thus, for example, in the injector arrangement described above with reference to FIGS. 4A and 4B, some of the seals between stages may need to withstand a pressure drop of 20 kpsi or even higher. Referring to FIG. 7, fluid at an input 160 of the injector may be at a first high pressure, P1, and fluid flowing out of the injector (indicated by arrow 162) may be at a much lower pressure, P2, resulting in the above-mentioned pressure drop across at least some of the seals. Conventional rotary valves and other seals have a high potential for developing some leakage, especially at high pressures and temperatures. To mitigate this leakage, the chamber surrounding the components may be filled with an inert gas at a pressure, P3, equal to or higher than the highest expected sample pressure. In one example, this gas may be carrier gas, which may eliminate the need for a separate carrier gas supply container or allow a smaller carrier gas supply container to be used. This can be seen with reference to FIG. 5 in which reference numeral 170 indicates the surrounding carrier gas. With this arrangement, any leakage past the "O"-ring seals (or other seals or valves) would introduce carrier gas into the fluidic path (rather than allowing sample to leak out). which in small proportions does not compromise the chromatographic analyses. In some embodiments, certain components of the gas chromatography system, for example, the sampler 122, may have internal cavities at pressures orders of magnitude different than P3. In such cases, these components (or portions thereof) can be encased in a localized housing having an internal pressure compatible with the device.

A chromatograph generally benefits from precise control and manipulation of the temperature of its major components. For example, the column may need to be heated and cooled cyclically for each analysis. The rate of heating may need to be fast for certain applications, while the rate of cooling preferably may be as fast as possible to minimize lag time between successive analyses. Certain analyses may require temperature ramping of the column while holding the injector and detector at a constant temperature. Also, the temperature distribution throughout the column, including its inlet and outlet, may preferably be uniform to maintain the quality of chromatographic separation. In many circumstances, the injector and the detector, as well as the fluidic interconnections, may also preferably need to be held at a controlled temperature to avoid cold spots and uneven thermal distribution. In conventional large-scale gas chromatography systems, thermal management is challenging and may be particularly difficult at high ambient temperatures. Even "miniaturized" fluidic connections used in traditional gas chromatography apparatus have large enough thermal mass, that thermal management becomes difficult at best.

Figure 8:
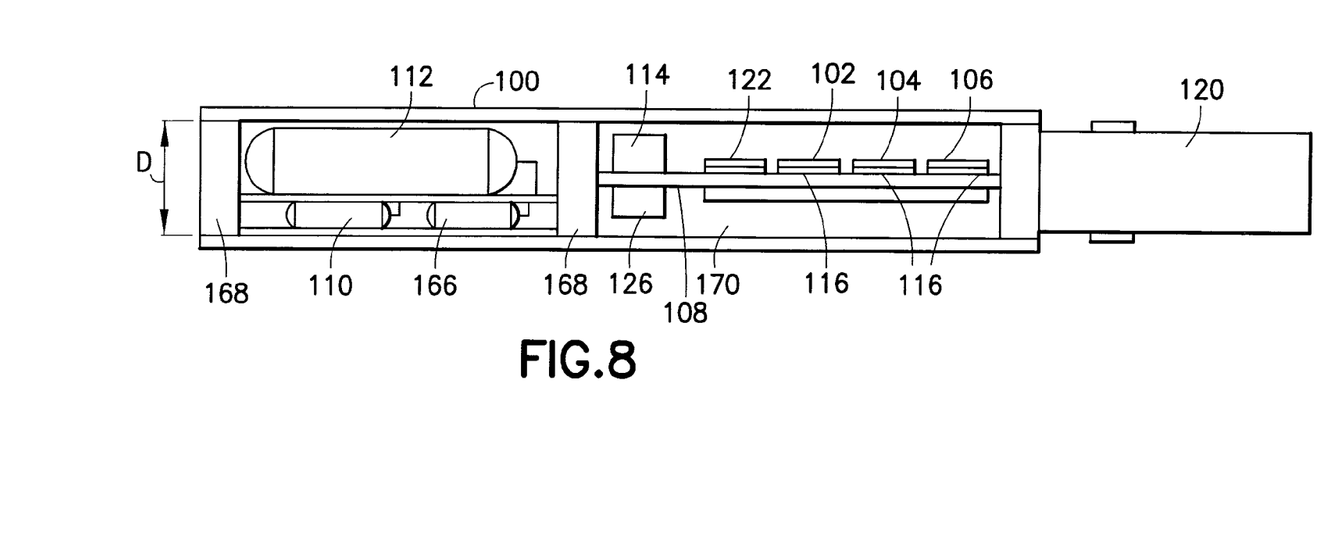
FIG. 8 is a block diagram of another embodiment of a gas chromatography system according to the invention.
Figure 9:
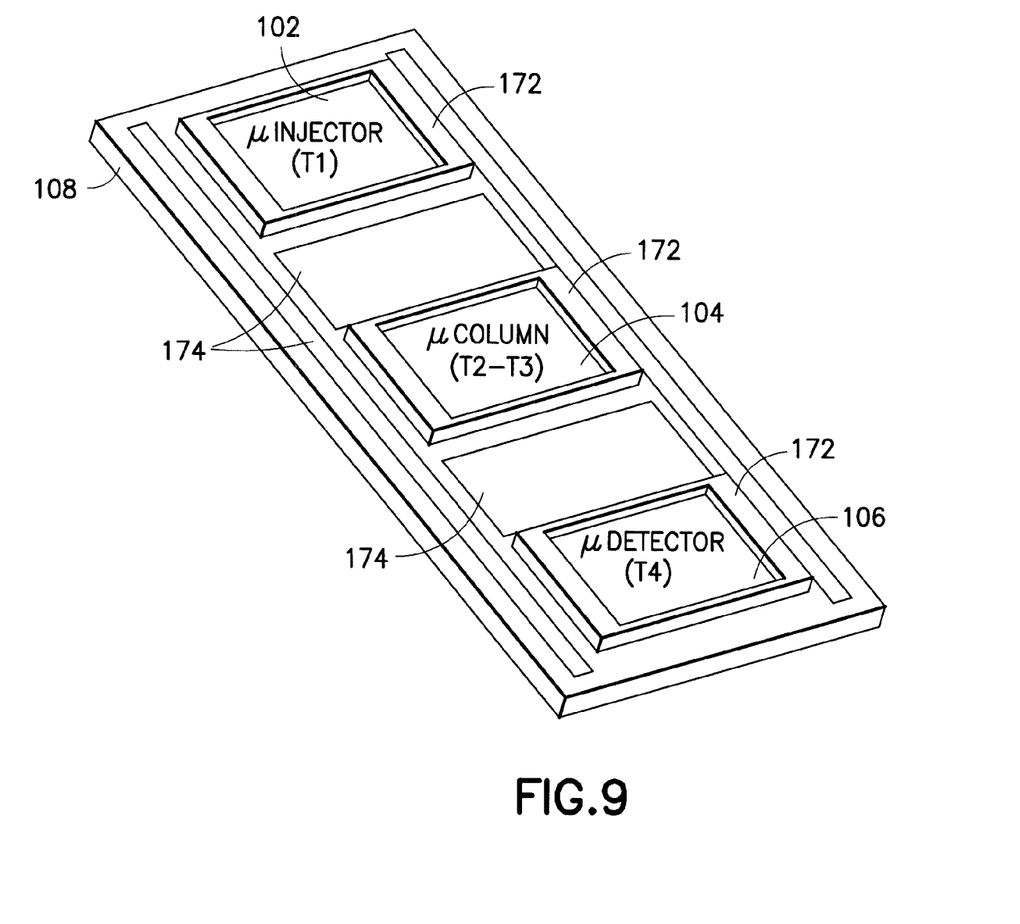
FIG. 9 is a perspective view of components of a gas chromatography apparatus including thermal management components according to an embodiment of the invention.

A micro-scale gas chromatography architecture according to embodiments of the invention may provide major advantages for effective thermal management. For example, the small size of micro-scale components equates to lower thermal mass. This may make temperature control of the components easier because there is a lower mass to be heated and/or cooled. According to one embodiment, the management of temperature transitions between components the injector, column and detector may be controlled by incorporation of thermal stops and traps, as shown in FIG. 9. FIG. 9 illustrates a micro-injector 102, micro-column 104 and micro-detector 106 coupled to the micro-fluidic platform 108 as well as thermal stops 172 and thermal traps 174. A thermal stop is a heated extra mass, sized to preserve the stability of temperature at the perimeter of the heated micro-device. A thermal trap, on the other hand, is a void filled with thermal insulator that limits heat transfer and thus heat loss from the isolated component. Each component may be provided with a heater 116 that may set a desired temperature, or provide a ramped temperature, for each component. Using the thermal stops and thermal traps, the uniformity of temperature within the heated components may be independently preserved. The heaters 116 may be, for example, ceramic heaters or Peltier devices. Peltier devices may be formed as a flat plate that may fit between a GC component and the micro-fluidic platform, as illustrated, for example, in FIGS. 2A-2C. Peltier devices have the property that when electricity is supplied, one side of the device heats up while the other side cools down. Thus, by providing a controlled supply of electricity (using the controls 114 and power supply 126 shown in FIG. 8) to a Peltier device, local heating and/or cooling may be provided for each GC component. For example, the injector may be operated at a first temperature, T1, the column operated over a range of temperatures, T2-T3, and the detector operated at a third temperature, T3 . These different temperatures may be maintained at the individual devices by using the heaters 116 together with the thermal traps and stops to isolate the devices from one another. With at least some of the GC components being at the micro-scale, such thermal management may be intrinsically easier to achieve.

Several environments have varying temperatures depending on ambient conditions such as depth underground or underwater. Specifically, the down-hole ambient temperature varies with depth. Therefore, according to another embodiment, a gas chromatography system that may be suitable for down-hole applications, or applications in other non-constant temperature environments, may include additional thermal management features. For example, temperature management of the GC components may be made more efficient by keeping the GC components in a thermally stable environment. To this end, referring again to FIG. 8, the housing 100 may be an isothermic container. For example, the housing 100 may be a tube constructed from Dewar Flask-like construction, for example, with mica insulated, layered construction. Such tubes are commercially available, and can optionally be rated to withstand down-hole external pressure. Using such as tube for the housing 100 may facilitate minimization of the heat transfer across the across the housing.

According to another embodiment, within the housing 100, several large thermal masses 168 may be incorporated. These thermal masses may be pre-cooled to stabilize the gas chromatography system at a pre-determined temperature before it is placed in service down-hole. The thermal masses 168 may help to maintain the internal temperature within a certain narrow range, despite changes in the external ambient temperature. In addition, the thermal masses 168 may help to maintain the internal temperature while the temperatures of the various components may be varied as needed to perform the analyses. Provided that the duty cycle of the GC apparatus is limited, these thermal masses may be sized reasonably to fit within a slender cylinder. As discussed above, temperature of individual components of the gas chromatography apparatus may be modulated using heaters 116. In one example, these heaters may be thermo-electric devices (Peltier devices) or ceramic heaters.

Referring again to FIG. 8. a cooling device 120 may be included in the gas chromatography system according to embodiments of the invention. In one example, the cooling device may be capable of operating at temperatures around 200° C. and providing a temperature reduction of about 100° C. One example of a suitable cooling device is a Sterling-cycle cooling device. Such a cooling device may provide a temperature delta of about 100° C. between "hot" and "cold" ends, both of which can be large thermal masses as discussed above. Using a correctly sized cooling device 120 in conjunction with a Dewar-style enclosure for the housing and thermal masses, an internal environment having an average temperature of less than about 100° C. can be created within the housing, despite high external ambient temperature. Such an internal temperature may be conducive to standard chromatographic analytical methods. The above-described arrangement, including the use of thermal masses, thermal traps and thermal stops, together with a cooling device, may be effective due the low thermal mass of micro-scale GC components compared to the rest of thermal management scheme described above.

In summary, according to various aspects and embodiments of the invention, a gas chromatography system may incorporate a common micro-fluidic platform that interconnects active GC components (e.g., an injector, column(s) and detector(s)) with nearly zero dead volume "tubeless" and "glueless" fluidic connections which reduces or eliminates "active spots," "cold spots" and sources of contamination, all of which would otherwise degrade the quality and/or reliability of measurements. At least some components of the system may be implemented at the micro-scale which, together with micro-flow channels in the fluidic platform, may allow for very low carrier gas consumption. As discussed above, the system may incorporate on-board waste management and carrier gas supply, as well as an on-board power supply (e.g., a battery), as shown in FIG. 8, allowing for self-contained operation. In at least some embodiments, the small size of components may allow the gas chromatography apparatus to be contained in a housing having an inner diameter, D, of about two (2) to three (3) inches, or even less, and a length of between about eight (8) inches and sixteen (16) inches, which is suitable for the geometric limitations of oil and gas wells. In some embodiments the system may incorporate a variety of thermal management components including a housing capable of providing a thermally stable environment, thermal traps and stops to thermally isolate individual components, heating and cooling devices and pre-heated or pre-cooled thermal masses that may provide additional thermal stability. Such a gas chromatography system may be capable of fast analysis times, for example, approximately one minute or less, due the small sample volume and small flow channels that may be used, as discussed above. In addition, the small thermal mass of micro-scale components may allow fast temperature cycling, allowing for a wait time between analyses of about two (2) minutes or less. Thus, embodiments of the invention may provide a compact, self-contained gas chromatograph having an architecture suitable for down-hole applications as well as applications in many other environments.

It is to be appreciated that the invention is not limited to the specific examples described herein and that the principles of the invention may be applied to a wide variety applications. The above description is therefore by way of example only, and includes any modifications and improvements that may be apparent to one of skill in the art. The scope of the invention should be determined from proper construction of the appended claims and their equivalents.

What is claimed is:

1. A gas chromatography system comprising:
a plurality of gas chromatography components;
means for individually controlling operating temperatures of at least one gas chromatography component of the plurality of gas chromatography components, wherein the means for individually controlling operating temperatures further includes thermal traps and thermal stops disposed about the plurality of gas chromatography components; and
a micro-fluidic platform coupled to the plurality of gas chromatography components to interconnect the plurality of gas chromatography components;
wherein the micro-fluidic platform comprises a plurality of flow channels that provide fluid flow paths for a sample, a carrier gas and a waste gas through and among the micro-fluidic platform and the plurality of gas chromatography components.

2. The gas chromatography system of claim 1, wherein the plurality of gas chromatography components includes an injector, at least one gas chromatography column and at least one detector.

3. The gas chromatography system of claim 2, further comprising a waste storage container coupled to the micro-fluidic platform and constructed and arranged to store the waste gas.

4. The gas chromatography system of claim 2, wherein the thermal traps and the thermal stops are disposed about the plurality of gas chromatography components so as to thermally isolate the plurality of gas chromatography components from one another.

5. The gas chromatography system of claim 2, further comprising a supply of the carrier gas coupled to an input of the at least one gas chromatography column.

6. The gas chromatography apparatus of claim 1, wherein controlling operating temperatures includes one of heating, cooling or both.

7. A gas chromatography apparatus comprising:
a micro-fluidic platform comprising a plurality of flow channels disposed thereon;
an injector coupled to the micro-fluidic platform and constructed and arranged to provide a sample for analysis;
a gas chromatography column coupled to the injector via the micro-fluidic platform and constructed and arranged to receive the sample from the injector and to produce an output dependent on a chemical composition of the sample;
a detector coupled to the gas chromatography column via the micro-fluidic platform and constructed and arranged to receive the output from the gas chromatography column;
means for individually controlling operating temperatures of one of the injector, the gas chromatography column or the detector, wherein the means for individually controlling operating temperatures further includes thermal traps and thermal stops disposed about the plurality of gas chromatography components; and
a housing substantially surrounding and enclosing the micro-fluidic platform, the injector, the gas chromatography column and the detector;
wherein the plurality of flow channels provide flow pathways for the sample and the output from the gas chromatography column.

8. The gas chromatography apparatus of claim 7, wherein at least one of the injector, the gas chromatography column and the detector is implemented at a micro-scale.

9. The gas chromatography apparatus of claim 7, wherein the injector, the gas chromatography column and the detector are anodically bonded to the micro-fluidic platform.

10. The gas chromatography apparatus of claim 7, further comprising a supply of carrier gas coupled to at least one flow channel of the plurality of flow channels.

11. The gas chromatography apparatus of claim 7, further comprising "O"-ring seals at coupling points between the flow channels and the injector, between the flow channels and the gas chromatography column and between the flow channels and the detector.

12. The gas chromatography apparatus of claim 11, wherein the housing is pressurized with a gas; and wherein the gas is carrier gas used in the gas chromatography column.

13. The gas chromatography apparatus of claim 7, further comprising a waste storage container coupled to the gas chromatography column and constructed and arranged to receive and store waste gas from the gas chromatography column.

14. The gas chromatography apparatus of claim 7, further comprising a calibration standard coupled to the injector to provide in situ calibration of the gas chromatography apparatus.

15. The gas chromatography apparatus of claim 7, wherein the housing is a Dewar flask housing.

16. The gas chromatography apparatus of claim 7, further comprising at least one heater coupled to at least one of the injector, the gas chromatography column and the detector to control an operating temperature of at least one of the injector, the gas chromatography column and the detector.

17. The gas chromatography system of claim 16, wherein the thermal traps and the thermal stops are disposed about the injector, the gas chromatography column and the detector and constructed and arranged to thermally isolate the injector, the gas chromatography column and the detector from one another.

18. The gas chromatography apparatus of claim 7, further comprising a Sterling-cycle cooling device coupled to the housing.

19. The gas chromatography apparatus of claim 7, wherein the housing is a cylindrical tube having has an inner diameter of less than about three inches.

20. The gas chromatography apparatus of claim 7, wherein the housing provides as a barrier of one of a external temperature, a external pressure or both external temperature and pressure.

21. The gas chromatography apparatus of claim 7, wherein the pressure in housing is equal to or higher than a pressure of the sample.

22. A gas chromatography system comprising:
a plurality of gas chromatography components;
a control means that individually controls operating temperatures for each component of the plurality of gas chromatography components such that the control means is constructed and arranged to thermally isolate each component of the plurality of gas chromatography components; and
a micro-fluidic platform coupled to the plurality of gas chromatography components to interconnect the plurality of gas chromatography components;
wherein the micro-fluidic platform comprises a plurality of flow channels that provide fluid flow paths for a sample, a carrier gas and a waste gas through and among the micro-fluidic platform and the plurality of gas chromatography components.

23. A gas chromatography system comprising:
a plurality of gas chromatography components;
a control means that individually controls operating temperatures for each component of the plurality of gas chromatography components such that the control means is constructed and arranged to thermally isolate each component of the plurality of gas chromatography components and provides controlling operating temperatures that includes one of heating, cooling or both; and
a micro-fluidic platform coupled to the plurality of gas chromatography components to interconnect the plurality of gas chromatography components;
wherein the micro-fluidic platform comprises a plurality of flow channels that provide fluid flow paths for a sample, a carrier gas and a waste gas through and among the micro-fluidic platform and the plurality of gas chromatography components.

* * * * *